(12) United States Patent
Bussett et al.

(10) Patent No.: US 11,623,031 B2
(45) Date of Patent: *Apr. 11, 2023

(54) OCCLUSIVE CHEST WOUND SEAL WITH A ONE-WAY VENT FOR PREVENTING AND TREATING TENSION PNEUMOTHORAX

(71) Applicant: Beacon Medical, LLC, Temecula, CA (US)

(72) Inventors: Gary R. Bussett, Vista, CA (US); Kyle H. Bussett, Vista, CA (US); Craig Lissner, Glencoe, IL (US)

(73) Assignee: Beacon Medical, LLC, Temecula, CA (US)

( * ) Notice: Subject to any disclaimer, the term of this patent is extended or adjusted under 35 U.S.C. 154(b) by 490 days.

This patent is subject to a terminal disclaimer.

(21) Appl. No.: 16/813,687

(22) Filed: Mar. 9, 2020

(65) Prior Publication Data
US 2020/0206398 A1     Jul. 2, 2020

Related U.S. Application Data

(63) Continuation of application No. 16/545,614, filed on Aug. 20, 2019, now Pat. No. 10,583,230, which is a
(Continued)

(51) Int. Cl.
*A61M 1/00* (2006.01)
*A61M 1/04* (2006.01)
(Continued)

(52) U.S. Cl.
CPC ......... *A61M 1/04* (2013.01); *A61F 13/00046* (2013.01); *A61F 13/00051* (2013.01);
(Continued)

(58) Field of Classification Search
CPC ............ A61M 1/90; A61M 2205/7536; A61M 1/962; A61M 1/74; A61M 1/912; A61M 1/964; A61M 2039/0276; A61M 2202/02; A61M 2205/15; A61F 13/00068; A61F 13/023; A61F 2013/00536; A61F 13/0226; A61F 13/0216; A61F 13/022; A61F 13/00046; A61F 13/00051; A61F 2013/00246
See application file for complete search history.

(56) References Cited

U.S. PATENT DOCUMENTS

2013/0296762 A1* 11/2013 Toth ................... A61F 13/0243
602/54

* cited by examiner

*Primary Examiner* — Kai H Weng
(74) *Attorney, Agent, or Firm* — K&L Gates LLP (57) ABSTRACT

A vented chest wound seal for a penetrating chest wound includes a flexible sheet including a top surface and a bottom surface, an adhesive hydrogel layer covering a portion of the bottom surface of the flexible sheet, and a plurality of vent channels. The adhesive hydrogel layer includes an inner perimeter and an outer perimeter, and the outer perimeter forms a continuous perimeter of hydrogel along a bottom surface of the flexible sheet. A plurality of vent channels, each including a first opening to a space inside of the inner perimeter, extend radially outward to an outer terminal end vent to the top surface of the flexible sheet. The outer terminal end is spaced apart from the outer perimeter of the adhesive hydrogel layer towards the central portion of the chamber.

13 Claims, 7 Drawing Sheets

Related U.S. Application Data continuation of application No. 14/704,311, filed on May 5, 2015, now Pat. No. 10,383,988.

(60) Provisional application No. 62/017,352, filed on Jun. 26, 2014, provisional application No. 61/989,845, filed on May 7, 2014.

(51) Int. Cl.
*A61F 13/00* (2006.01)
*A61F 13/02* (2006.01)
*A61M 39/02* (2006.01)

(52) U.S. Cl.
CPC ....... *A61F 13/00068* (2013.01); *A61F 13/022* (2013.01); *A61F 13/023* (2013.01); *A61F 13/0216* (2013.01); *A61F 13/0226* (2013.01); *A61F 2013/00246* (2013.01); *A61F 2013/00536* (2013.01); *A61M 1/74* (2021.05); *A61M 1/90* (2021.05); *A61M 1/962* (2021.05); *A61M 1/964* (2021.05); *A61M 2039/0276* (2013.01); *A61M 2202/02* (2013.01); *A61M 2205/15* (2013.01); *A61M 2205/7536* (2013.01)

OCCLUSIVE CHEST WOUND SEAL WITH A ONE-WAY VENT FOR PREVENTING AND TREATING TENSION PNEUMOTHORAX

CROSS-REFERENCE TO RELATED APPLICATIONS

This application is a continuation of, incorporates by reference, and claims the benefit of priority to U.S. patent application Ser. No. 16/545,614 filed on Aug. 20, 2019, which is a continuation of U.S. patent application Ser. No. 14/704,311 filed on May 5, 2015, which is a non-provisional utility patent application incorporating by reference and claiming the benefit of priority to U.S. Provisional Patent Application No. 61/989,845 filed May 7, 2014, and U.S. Provisional Patent Application No. 62/017,352 filed Jun. 26, 2014.

BACKGROUND OF THE INVENTION

The present subject matter relates generally to a chest wound seal for first responders. More specifically, the present invention relates to a chest wound seal that stores compactly, includes: four-sided sealing; a one-way venting valve with no rigid components; and a one-way valve and vent channel resistant to blockage from clotting; and, additionally, a chest wound seal that may be thin; flexible; conformal to body contours; aggressively adhesive to contaminated surfaces (stick and stay); highly resistant to externally-originated particulate contamination; functional when covered with patient's clothing; and configurable as venting or non-venting.

When an individual suffers a puncture wound to the chest, such as from being shot or stabbed, the wound often penetrates into the chest cavity so as to puncture the parietal pleura, visceral pleura, and sometimes even the lungs. Such a wound allows air to flow freely through the open chest wound into the chest cavity and pleural space each time the patient breathes.

The condition wherein air penetrates into the pleural space between the lung and the chest wall through a wound hole in the chest wall is an open pneumothorax. When an open pneumothorax occurs, the normal mechanism by which the lung expands is lost; i.e., the fluid adhesion of the pleural surface of the lung to the pleural surface of the chest wall. Thus, the affected lung does not expand normally when the patient inhales.

A tension pneumothorax can occur when a one-way valve is formed by the wound that allows airflow into the pleural space while preventing airflow out. In a tension pneumothorax, each inhalation traps air in the chest, increasing pressure on the lungs and ultimately causing them to collapse. Additionally, the increasing pressure pushes important organs, such as the heart, major blood vessels, and airways, toward the center of the chest. This shifting can cause further compression of the lungs and may affect the flow of blood returning to the heart. These additional complications in a tension pneumothorax make it a life threatening condition that requires immediate treatment.

For patients with an open wound to the chest, the severity of the open pneumothorax that develops can be minimized by sealing the open wound via an occlusive bandage. For proper sealing, the bandage must be air- and liquid-tight, must be flexible enough to conform to all body contours, and must have an adhesive strong and persistent enough to keep the seal in place while subject to patient movement and various body fluids. The occlusive bandage may be used to eliminate air penetrating into the pleural space through the wound hole when the patient inhales.

In addition to developing a tension pneumothorax by air leakage through the chest wound, a patient with an open chest wound that is covered by an occlusive chest bandage may also develop a tension pneumothorax in a different manner. For instance, the bandage may have eliminated air from entering the pleural space through the wound hole, yet if lacerated, the lung will continue to leak air into the pleural space. Consequently, every time the patient inhales, more air becomes trapped in the pleural space, causing more pressure to be exerted on the lacerated lung. Again, this increased pressure on the lacerated lung forces the lung to collapse.

To successfully prevent a tension pneumothorax from developing, the air flow into the pleural space via the wound hole must be eliminated, but the air coming from the lacerated lung must be allowed to escape the pleural space via the wound hole.

Therefore, a need exists for a compact, low profile, adhesive chest wound seal for use by first responders that includes a one-way valve that ensures effective venting of air and/or other fluids from the pleural cavity during exhalation while sealing a chest wound against air entry during inhalation, without risk of being dislodged during treatment of the patient.

U.S. Pat. No. 5,478,333 to Asherman ("Asherman") discloses a one-way valve apparatus installed in a chest wound seal to be used for treating a tension pneumothorax, as well as treat hemothorax (blood accumulation in the pleural cavity). The adhesive used on Asherman fails when exposed to bodily fluids such as blood or sweat. If the adhesive fails, then Asherman will not exhibit a 4-sided seal, rendering its air-ingress-during-inhalation-prevention function useless.

In addition, the design of Asherman will only allow air egress during exhalation if the valve apparatus is free of encumbrances, such as clothing, impinging on the valve exit end. Such interference will kink the valve shut, rendering it inoperative, and thereby turning Asherman into a simple occlusive chest wound seal. Further, Asherman will also not vent if the patient is lying upon the chest wound/vent, which will also kink the vent exit. Such a condition will prevent air ingress during inhalation, but will also prevent air/fluid egress during exhalation, a situation that can lead to formation of a life-threatening tension pneumothorax.

U.S. Pat. No. 7,504,549 to Castellani et al. ("Hyfin") discloses a one-way valve fabricated as an integral part of a thin, flexible chest wound seal that claims to prevent tension pneumothorax. Hyfin discloses that its drainage channel terminates at the peripheral edge of the chest wound seal. The lack of a full perimeter of adhesive (hydrogel) in combination with a thin and flexible backing sheet can allow the Hyfin to fold along its drainage channel and allow the two sides of that channel to contact each other during Hyfin application, causing the channel to close upon itself. The hydrogel is aggressively sticky, and once stuck to itself, cannot easily be separated to reopen the occlusion in the channel.

U.S. Pat. No. 7,834,231 to Biddle et al. ("Biddle") discloses a plurality of one-way valve apparati installed in a thin, flexible chest wound seal that claims to prevent tension pneumothorax. Biddle contains a one-way valve with a fibrous filter in line with the air flow path. The limited clear egress fluid path will be prone to blockage if the blood from the chest wound clots. Clotting will render Biddle a simple occlusive chest wound seal.

In addition, the one-way valve mechanism is subject to interference by externally originated particulate contamination, which can prevent valve closure during inhalation. If a valve fails to seal during inhalation, air can enter the pleural space through the chest wound and cause the formation of a life-threatening tension pneumothorax.

U.S. Pat. Appl. No. US 2012/0046582 to Hopman et al. ("Hopman")—discloses a one-way valve apparatus installed in a chest wound seal that claims to prevent tension pneumothorax. The Hopman valve is a rigid, bulky one-way valve apparatus. The Hopman valve is susceptible to externally originated particulate contamination, which can prevent valve closure during inhalation. If the valve fails to seal during inhalation, air can enter the pleural space through the chest wound and cause the formation of a life-threatening tension pneumothorax.

The one-way valve can be protected from external contaminants by replacing its removable cover, but with the cover in place, the vent is rendered inoperative, thereby turning Hopman into a simple occlusive chest wound seal. Such a condition will prevent air ingress during inhalation, but will also prevent air/fluid egress during exhalation, a situation that can lead to formation of a life-threatening tension pneumothorax.

In addition, the rigid, bulky one-way valve apparatus of Hopman protrudes approximately ⅝ of an inch above the top surface of the chest wound seal. This bulkiness ensures that fewer of the units can be carried in first responder kits than other thinner, more flexible chest wound seals.

Accordingly, there is a need for a chest wound seal for first responders that stores compactly, includes: four-sided sealing; a one-way venting valve with no rigid components; and a one-way valve and vent channel resistant to blockage from clotting; and, additionally, is thin; flexible; conformal to body contours; aggressively adhesive to contaminated surfaces (stick and stay); highly resistant to externally-originated particulate contamination; functional when covered with patient's clothing; and configurable as venting or non-venting, as described herein.

BRIEF SUMMARY OF THE INVENTION

To meet the needs described above and others, the present disclosure provides a chest wound seal for first responders that stores compactly and includes: four-sided sealing; a one-way venting valve with no rigid components; and a one-way valve and vent channel resistant to blockage from clotting. Additionally, the present disclosure provides a chest wound seal for first responders that is: thin; flexible; conformal to body contours; aggressively adhesive to contaminated surfaces (stick and stay); highly resistant to externally-originated particulate contamination; functional when covered with patient's clothing; and configurable as venting or non-venting.

The present invention satisfies the objectives by providing a chest wound seal that is an occlusive dressing for use on a penetrating chest wound that may be used to treat an open pneumothorax and/or to prevent a tension pneumothorax. The chest wound seal contains a one-way valve that allows air and/or other fluids to exit the pleural space during exhalation but blocks air from entering the pleural space during inhalation. The chest wound seal, by the inclusion of these two functions of the one-way valve, may be used to treat an open pneumothorax and prevent a tension pneumothorax.

The chest wound seal may include several thin layers in a novel arrangement that together become an integrated one-way valve that ensures effective venting of air and/or other fluids from the pleural cavity. The chest wound seal may be thin to render it unobtrusive during use on a patient. The thinness also enables a low-volume package, which allows many units to be carried in a small volume. The chest wound seal may also include an integrated one-way valve that may be resistant to the effects of externally originated particulate contamination, which ensures the aforementioned effective venting of air or other fluids from the pleural cavity during exhalation and reliable sealing against air ingress during inhalation.

The chest wound seal uses an aggressively sticky hydrogel as its adhesive, which exhibits excellent adhesion properties even on surfaces that are contaminated with blood, hair, or other bodily fluids. The strong adhesion minimizes the risk of the chest wound seal being dislodged during treatment or movement of the patient.

The chest wound seal's one-way valve doesn't protrude above the top surface of the chest wound seal, which helps ensure that it will function correctly when covered with the patient's clothing.

The chest wound seal employs no fibrous filters in the vent path, which reduces the likelihood of blockage due to clotting at the filter.

The chest wound seal's one-way valve employs a large sealing surface that contains no rigid components. This feature of the chest wound seal renders it highly resistant to interference from externally originated particulate contamination, which ensures that it will function correctly in the presence of said particulate contamination.

The chest wound seal includes a vent channel that does not require the undesirable elimination of the adhesive hydrogel at the peripheral edge of the chest wound seal. The unique design of the vent permits hydrogel adhesive to completely surround the chest wound, thereby providing a full 360-degrees sealing, or a "four-sided" seal. The presence of adhesive gel all the way around the chest wound seal's perimeter also provides added rigidity in the area of the vent channel during application to the patient. That added rigidity reduces the likelihood of accidental folding of the chest wound seal along its vent channel, having the two sides of the channel touch and stick together, and blocking the channel.

One embodiment of the chest wound seal includes a removable adhesive member that blocks the vent opening. That blocking member is intended for use when a non-vented chest wound seal is desired. The blocking member may be only a few mils thick, and when present is unobtrusive and flexible. Its presence does not add bulk to the chest wound seal. That lack of additional bulk allows the use of the same small packaging, ensuring that more of the units can be carried in first responder kits than other thicker, less flexible chest wound seals.

In one embodiment, the chest wound seal includes: a thin, flexible, plastic backing sheet; an adhesive sheet with an inner perimeter defining a chamber and a channel; and a vent hole in the thin, flexible plastic sheet. To enable use of the chest wound seal, the chest wound seal includes: a lifting tab integral with the thin plastic sheet; a release strip on an edge of the adhesive sheet at a base of a lifting tab; and a release liner to be removed before application.

Optionally, the chest wound seal may include a removable adhesive vent hole cover that blocks the vent exit, thereby establishing the initial configuration of the chest wound seal as a non-vented chest wound seal. Removal of the adhesive vent hole cover converts the non-vented chest wound seal into a vented chest wound seal, with all the aforementioned benefits of a vented chest wound seal.

The chest wound seal may come packaged in a sealed, vacuum-packed, plastic envelope that may be sterile. The flatness and flexibility of the package and the chest wound seal, allow the packaged chest wound seal to be folded or rolled to allow storage in a small space. Alternatively, the chest wound seal may be distributed in bulk unpackaged and unsterilized.

To use the chest wound seal the user must tear open the sealed, vacuum-packed, sterile plastic envelope, if so packaged, and remove the chest wound seal. If the chest wound seal is folded inside the packaging, it must be unfolded. The user must locate the chest wound on the patient. If possible, the user should clean the area around the chest wound at least four inches from the wound of blood, sweat, dirt, and any loose debris, in order to ensure adequate adhesion of the chest wound seal. After the wound is cleaned the user must grasp the lifting tab with one hand and remove and discard the removable release liner from the chest wound seal with the other hand. The chest wound seal must be applied over the patient's wound, adhesive side down, centered over the wound.

Once applied, the one-way valve contained in the chest wound seal operates as described to permit venting through the penetrating chest wound of air and/or other fluids from the pleural space during exhalation, thereby preventing tension pneumothorax. During inhalation, the one-way valve contained in the chest wound seal blocks air from entering the pleural space via the penetrating chest wound.

In an embodiment, a vented chest wound seal for a chest wound includes: a flexible sheet including a bottom surface; and an adhesive layer covering a portion of the bottom surface of the flexible sheet, the adhesive layer including an inner perimeter and an outer perimeter, the inner perimeter defining a chamber; wherein the chamber includes a vent channel extending radially outward from a central portion of the chamber, wherein the flexible sheet includes a vent hole aligned over the vent channel, and wherein the inner perimeter and the outer perimeter are separated by a minimum hydrogel width.

In an embodiment, the chest wound seal further includes: a lifting tab integrally formed with the flexible sheet; a plastic support sheet secured to the lifting tab to provide support; and a narrow release strip applied over a bottom surface of an edge of the adhesive layer closest to the lifting tab.

In an embodiment, the chest wound seal further includes: a lifting tab integrally formed with the flexible sheet; a plastic support sheet secured to the lifting tab to provide support; wherein a portion of the plastic support sheet is applied over a bottom surface of an edge of the adhesive layer closest to the lifting tab.

In an embodiment, the chest wound seal further includes a vent hole cover, wherein the vent hole cover includes an adhesive surface and a pull tab, wherein the adhesive surface secures the vent hole cover over the vent channel. In some embodiments, the chamber further includes a second vent channel extending radially outward from the central portion of the chamber, wherein the flexible sheet includes a second vent hole aligned over the second vent channel. And, in some embodiments, the chamber further includes a third vent channel and a fourth vent channel extending radially outward from the central portion of the chamber, wherein the flexible sheet includes a third vent hole aligned over the third vent channel, and a fourth vent hole hold aligned over the fourth vent channel.

In some embodiments, the vent channel extends a length from a center of the chamber to a terminus, wherein a shape of the terminus of the vent channel is approximately semi-circular. Additionally, in some embodiments, a length from a center of the chamber to a center of the vent hole is in the range of one to two and a half inches. Also, in some embodiments, the length from the center of the chamber to the center of the vent hole is in the range of one and one fourth inches to two inches. Further, in some embodiments, the length from the center of the chamber to the center of the vent hole is approximately one and a half inches.

In some embodiments, the minimum hydrogel width is one-half inch or greater. And, in some embodiments, the minimum hydrogel width is approximately one-inch. Further, in some embodiments, the vent channel is approximately three-fourths of an inch wide.

Some objects of the invention are to provide a chest wound seal for first responders that is: thin; flexible; and conformal to body contours.

Additional objects of the invention are to provide a chest wound seal for first responders that includes four-sided sealing; is highly resistant to externally-originated particulate contamination; is functional when covered with patient's clothing; is configurable as venting or non-venting; and stores compactly.

Further objects of the invention are to provide a chest wound seal for first responders that includes aggressive adhesion to contaminated surfaces (stick and stay); includes a one-way venting valve with no rigid components; and includes a one-way valve and vent channel resistant to blockage from clotting.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE INVENTION

Figure 1:
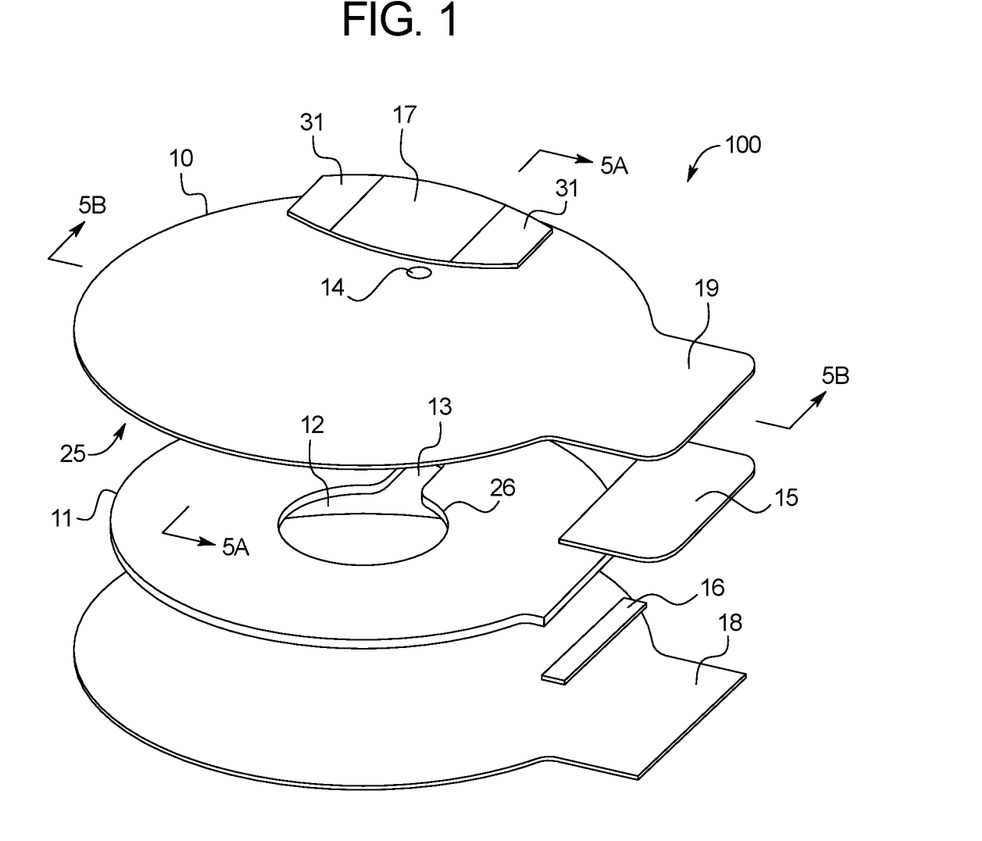
FIG. 1 illustrates an exploded isometric view of the vented chest wound seal that is one embodiment of the chest wound seal disclosed herein.
Figure 5A:
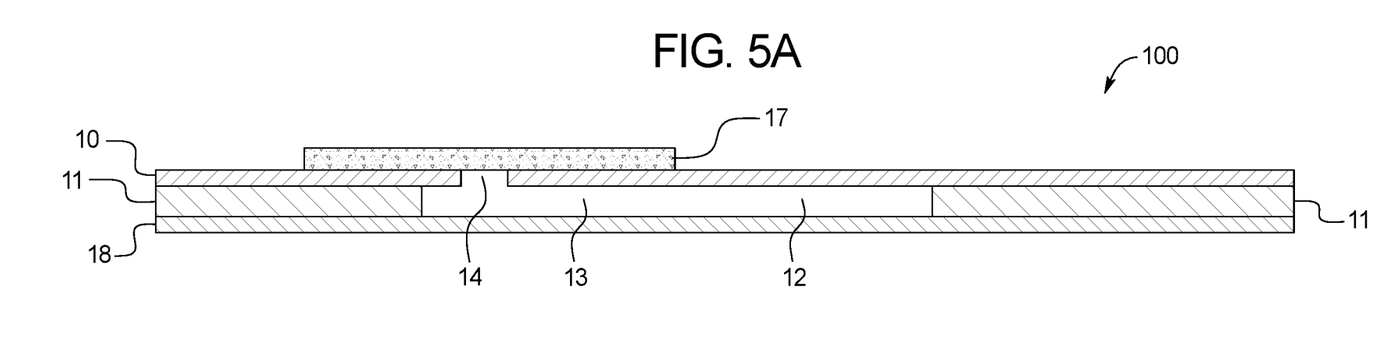
FIG. 5A illustrates a sectional view, not to scale, with some details enlarged to show their details, taken along Line 5A-5A of FIG. 1.
Figure 5B:
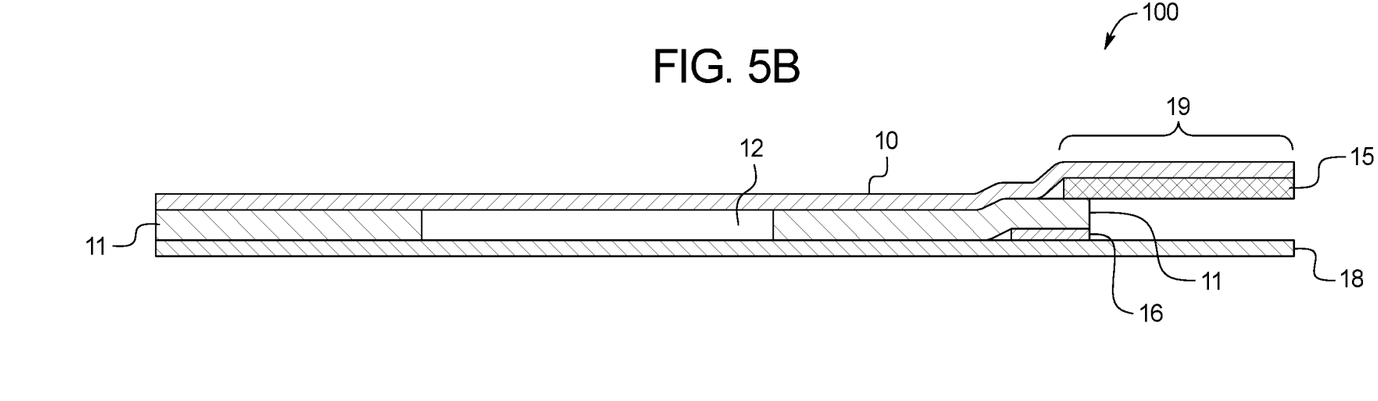
FIG. 5B illustrates a sectional view, not to scale, with some details enlarged to show their details, taken along Line 5B-5B of FIG. 1.
Figure 6:
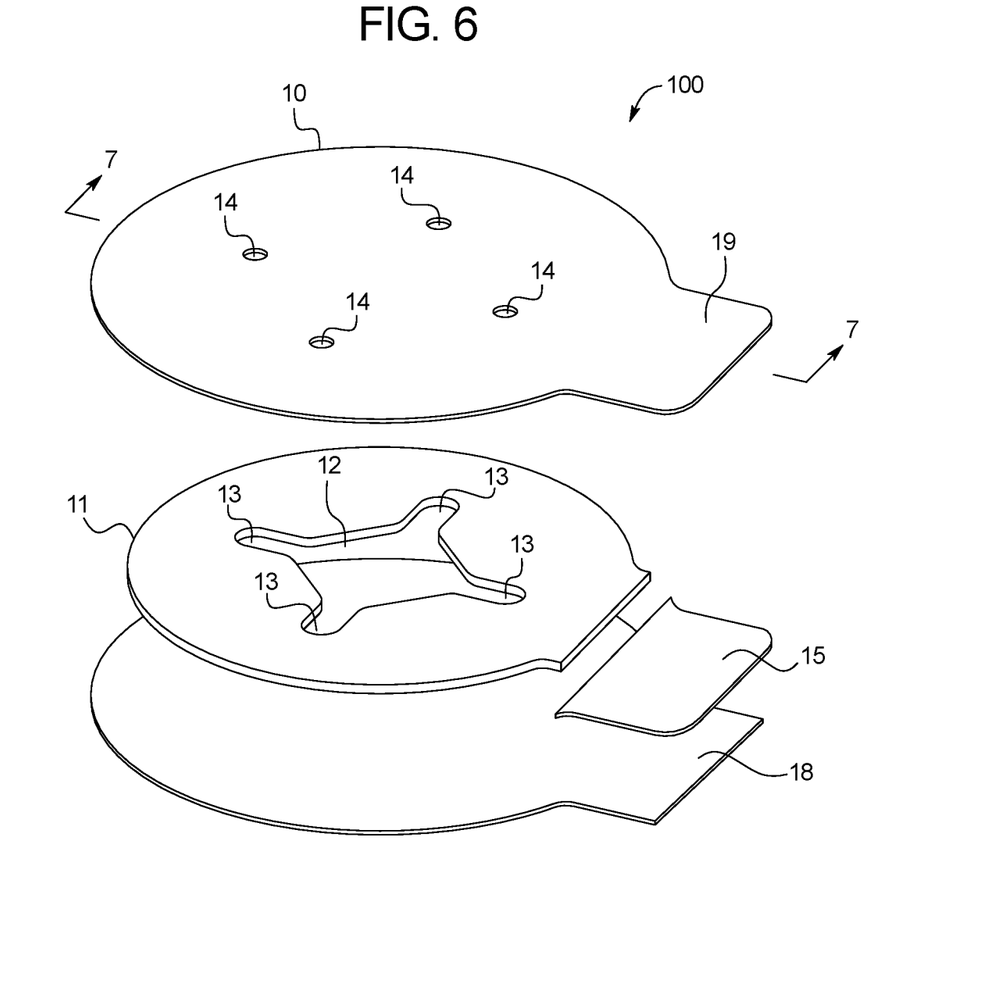
FIG. 6 illustrates an exploded isometric view of another example of a vented chest wound seal.

FIG. 1 illustrates an exploded isometric view of an example vented chest wound seal 100. FIG. 6 illustrates an exploded isometric view of another example of the chest wound seal 100. FIG. 5A is a sectional view, not to scale, with some details enlarged to show their details, taken along Line 5A-5A of FIG. 1. FIG. 5B is a sectional view, not to scale, with some details enlarged to show their details, taken along Line 5B-5B of FIG. 1.

With reference to FIG. 1, FIGS. 5A and 5B, a chest wound seal 100 for use as an occlusive dressing for a penetrating chest wound is shown. In an embodiment, the chest wound seal 100 may include a thin, flexible backing sheet 10 with a layer of hydrogel adhesive, referred to herein as a hydrogel adhesive sheet 11, covering a portion of a bottom surface 25 of the backing sheet 10. The adhesive sheet 11 may include an inner perimeter 26 and an outer perimeter 27. The inner perimeter 26 may define a chamber 12 and a vent channel 13 that lack hydrogel adhesive. A vent hole 14 may be included in the backing sheet 10 and may be aligned with the end geometry of the vent channel 13. The thin, flexible backing sheet 10, hydrogel adhesive sheet 11, chamber 12, vent channel 13, and vent hole 14 constitute a one-way valve of the chest wound seal 100 to permit air and/or other fluids 22 (FIG. 4A) to exit a penetrating chest wound 20 (FIG. 3A) during exhalation.

As described below with reference to FIGS. 3A-4B, the chamber 12 may be adapted to be centered and placed over the penetrating chest wound 20. The thin flexible backing sheet 10 may be transparent so that the chamber 12 of the chest wound seal 100 may be positioned centered over the penetrating chest wound 20 and so that the open chest wound 20 may be visually monitored. A larger chamber 12 makes it easier for the first responder to properly position the chamber 12 over the chest wound 20. In an embodiment, the chamber 12 is in the range of one inch to two inches in width. In a preferred embodiment, the chamber is a square approximately two inches wide. In other embodiments, the chamber 12 may be different sizes or shapes in order to accommodate different functional requirements.

The backing sheet 10 may be impermeable to air and water-based liquids, and should conform and seal over and around debris and irregularities on its mounting surface. Accordingly, it has been observed that flexibility and conformability are the key characteristics to consider for the flexible backing sheet 10. Maximizing these two characteristics provides optimal operation of the one-way valve. In an embodiment, the flexible backing sheet 10 includes urethane. In other embodiments, other flexible plastics or similar materials may be used, as will be apparent to those of skill in the art from the disclosure herein.

It has been observed that the hydrogel of the adhesive sheet 11 should be as sticky as possible in order to adhere to skin that may be contaminated with blood, sweat, dirt or hair. In an embodiment, the adhesive sheet 11 is constructed from hydrogel adhesive sold commercially as KM10E Katecho Gel, 0.032" by Katecho, Inc. of Des Moines, Iowa. In other embodiments, other hydrogel adhesives may be used as will be appreciated by those skilled in the art from the examples provided herein.

The chest wound seal 100 may also include the adhesive-backed plastic support sheet 15 that may be to be used to provide support to a lifting tab 19, a narrow strip of plastic sheet that may be used as a release strip 16, an adhesive-backed vent hole cover 17, and an additional plastic sheet that may be used as a removable release liner 18. The lifting tab 19 may be provided in the shape of a square, semicircle, rectangle, triangle, etc. In an embodiment, the lifting tab 19 is rectangle integrally formed with the backing sheet 10 and is of a size that can be gripped by at least two fingers. In a preferred embodiment, the lifting tab 19 is rectangular at two and three-fourths inches wide by one and a half inches deep. These dimensions are considered large enough to enable grasping by any of the several tested one-handed methods using either a thumb or heel of the hand and one, two, three, or four fingers.

The adhesive backed vent hole cover 17 may include a strip of plastic including an adhesive portion and a non-adhesive portion. The adhesive portion may secure the vent hole cover 17 to the backing sheet 10 while the non-adhesive portion acts as a pull-tab 31 that may be used for removal of the vent hole cover 17. Removal of the vent hole cover 17 converts the chest wound seal 100 from a non-vented occlusive chest wound seal 100 into a vented occlusive chest wound seal 100 that may be suitable for treatment of an open pneumothorax and prevention of a tension pneumothorax. In embodiments including a plurality of vent holes 14, a plurality of vent hole covers 17 may be provided to cover each vent hole 14. Alternatively, in some embodiments, a single vent hole cover 17 may cover a plurality of vent holes 14.

The vent channel 13 provides separation between the chamber 12 and the vent hole 14. If the vent hole 14 is positioned over the chest wound 20, the vent hole 14 will prevent the sealing of the flexible backing sheet 10 against the patient's chest 21. A longer vent channel 13 will minimize the likelihood of this occurrence. A vent channel length of the vent channel 13 extends from a central portion 28 of the chest wound seal 100 to a terminus 30.

In an embodiment, a possible range for vent channel length is one inch (providing the maximum minimum hydrogel width 29 between the inner perimeter 26 and the outer perimeter 27 at the cost of a high danger of non-sealing due to poor placement of the chamber 12) to two and a half inches (maximum vent hole separation while reducing the minimum hydrogel width 29 to a sliver). In other embodiments, the vent channel length is at least one-and-one fourth inches or greater to two inches. In a preferred embodiment, the vent channel 13 is approximately one and one half inches long, which is a compromise between the risk of non-sealing and providing an adequate minimum hydrogel width 29 of the adhesive sheet 11. The minimum hydrogel width 29 ensures a strong and persistent 360-degrees seal around the penetrating chest wound 20 to minimize the risk of the chest wound seal 100 being dislodged during treatment or movement of the patient.

The width of the vent channel 13 may also be adapted to improve venting. A wide vent channel 13 allows air to vent easily with minimal backpressure produced. A wide vent channel 13 is also more tolerant of clotting, which will narrow the channel width and impede airflow. In an embodiment, the vent channel 13 is approximately three-fourths of an inch wide, which is three times the size of the vent hole 14. Accordingly, clotting would have to reduce the vent channel by two-thirds (a reduction of a half-inch) before the venting function is affected.

The vent channel 13 is superior to prior approaches. For example, unlike prior chest wound seals with a drainage channel that terminates at the peripheral edge of the chest wound seal, the chest wound seal 100 includes adhesive gel along the full perimeter of the backing sheet 10 (with the exception of the lifting tab 19). A drawback of the drainage channel chest wound seals is the risk of the two sides of the channel creeping or migrating towards each other, pinching off the flow of the air and/or other fluids 22. An advantage of the present chest wound seal is that the geometry of the vent channel 13 (such as its semi-circular shape), as defined by the hydrogel of the adhesive sheet 11, keeps the walls of the vent channel 13 separated, reducing the likelihood of the channel walls touching each other, sticking together, and becoming blocked.

Additionally, the drainage channel chest wound seals, with no gel along the channel axis, have a gel-free path all the way to the perimeter of the seal, greatly increasing the likelihood that the seal will fold at the channel and stick to itself. The hydrogel at the terminus 30 (FIGS. 2A and 2B) of the vent channel 13 of the disclosed chest wound seal 100 provides added chest wound seal rigidity, which reduces the likelihood of inadvertent folding.

With reference to FIGS. 2A, 2B, 2C, and 2D some alternate embodiments are shown. The alternate embodiments show some possible orientation angles between the vent channel 13 and the lifting tab 19 along with variation in the number of vent channels 13. In each embodiment the chamber 12 and vent channel 13 are defined by the removal of or absence of hydrogel adhesive in the adhesive sheet 11. In each of the embodiments the vent channel 13 extends radially outward from a central portion 28 of the chamber 12, an arrangement that may be the optimum arrangement for the venting of air and/or other fluids 22 from the penetrating chest wound 20 through the vent hole 14.

Figure 2A:
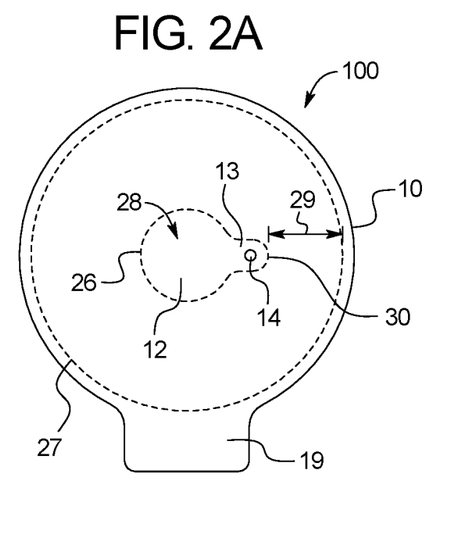
FIG. 2A illustrates a top plan view of one embodiment of the chest wound seal showing the orientation angle between the vent channel and the lifting tab. The optional vent hole cover is removed in order to clearly show the vent channel and vent hole.

FIG. 2A is a top plan view of one embodiment of the chest wound seal 100 showing the orientation angle between the vent channel 13 and the lifting tab 19. The vent hole cover 17 may be removed in order to clearly show the vent channel 13 and vent hole 14. As shown, the vent channel 13 extends radially outward from a central portion 28 of the chamber 12 to the terminus 30. The chamber 20 and the vent channel 13 are defined by the inner perimeter 26 of the adhesive sheet 11. The portion of the adhesive sheet 11 from the terminus 30 to the outer perimeter 27 may be a minimum hydrogel width 29 to provide stability to the chest wound seal 100. A wider minimum hydrogel width 29 is desired to maximize perimeter adhesion. In an embodiment, to provide stability to the adhesive sheet 11, the minimum hydrogel width 29 is one-half inch or greater. In an embodiment, to provide a sufficient trade-off between the length of the vent channel 13 and the stability of the chest wound seal 100, the minimum hydrogel width 29 is approximately one-inch.

Figure 2B:
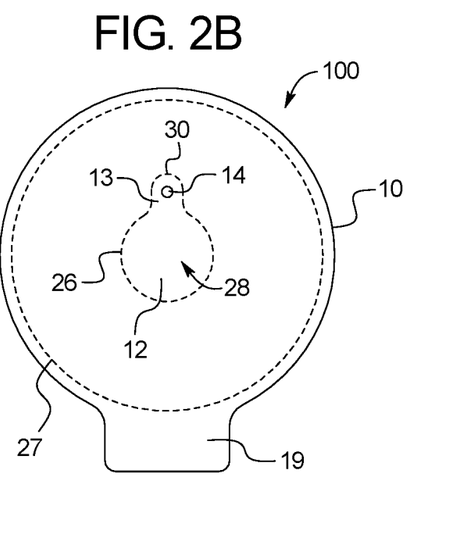
FIG. 2B illustrates a top plan view of an alternate embodiment of the chest wound seal showing a different orientation angle between the vent channel and the lifting tab. The optional vent hole cover is removed in order to clearly show the vent channel and vent hole.

FIG. 2B is a top plan view of an alternate embodiment of the chest wound seal 100 showing a different orientation angle between the vent channel 13 and the lifting tab 19. No vent hole cover 17 is shown in this embodiment. In a preferred embodiment of the chest wound seal 100 shown in FIG. 2B, no vent hole cover 17 is provided.

Figure 2C:
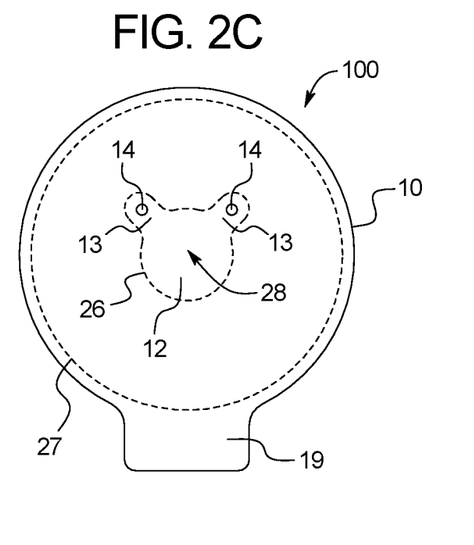
FIG. 2C illustrates a top plan view of another alternate embodiment of the chest wound seal showing two vent channels and other different orientation angles between the vent channels and the lifting tab. The optional vent hole covers are removed in order to clearly show the vent channels and vent holes.
Figure 2D:
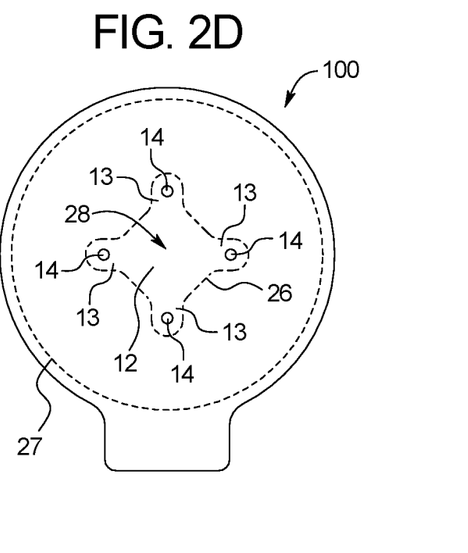
FIG. 2D illustrates a top plan view of another alternate embodiment of the chest wound seal showing four vent channels. The optional vent hole covers are removed in order to clearly show the vent channels and vent holes.

FIG. 2C is a top plan view of another alternate embodiment of the chest wound seal 100 showing two vent channels 13 and other different orientation angles between the vent channels 13 and the lifting tab. Similarly, FIG. 2D is a top plan view of another alternate embodiment of the chest wound seal 100 showing four vent channels 13 and other different orientation angles between the vent channels 13 and the lifting tab 19. In this embodiment, the vent channels 13 form a cross pattern. More vent channels 13 provides redundant venting in case one or two vent channels 13 become blocked. It is contemplated that the chest wound seal 100 may have as many as eight vent channels 13 and still function properly. In an embodiment, the chest wound seal 100 includes four channels because more than four vent channels 13 offers diminishing returns to redundancy.

Figure 3A:
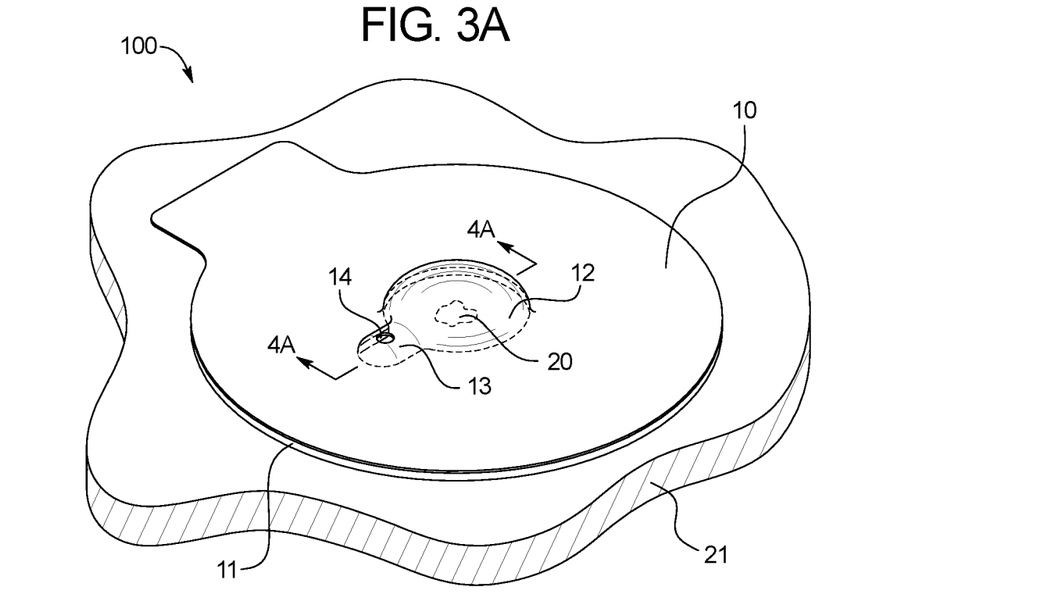
FIG. 3A illustrates an isometric view of the chest wound seal applied to a penetrating chest wound and allowing air and/or other fluids to vent from the wound through the open one-way valve during exhalation.
Figure 4A:
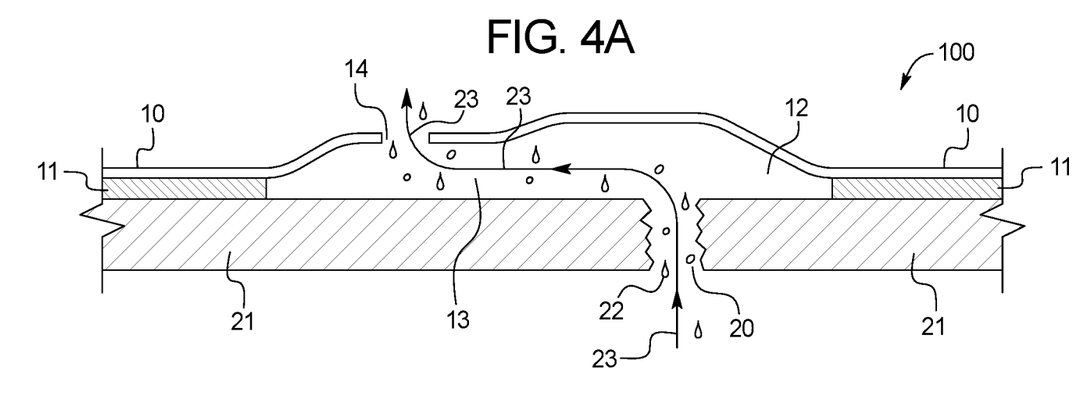
FIG. 4A illustrates a sectional view at an enlarged scale taken along Line 4A-4A of FIG. 3A.

With reference to FIG. 3A and FIG. 4A, the one-way valve of the chest wound seal 100 is shown in its venting state. FIG. 3A illustrates an isometric view of the chest wound seal 100 applied to a penetrating chest wound 20 and allowing air and/or other fluids to vent from the chest wound 20 through the vent hole 14 during exhalation. FIG. 4A illustrates a sectional view at an enlarged scale taken along Line 4A-4A of FIG. 3A. Chamber 12 and vent channel 13 are in an open position, with the thin, flexible backing sheet 10 shown as pushed away from the surface of the patient's chest 21 by air and/or other fluids 22 exiting the penetrating chest wound 20 during exhalation. The exhaled air and/or other fluids 22 are flowing outward in the direction shown by the flow arrow 23 from the penetrating chest wound 20 through the chamber 12 and vent channel 13 and exiting through the vent hole 14. The exiting of air and/or other fluids through the one-way valve results in the treatment and reduction in severity of the tension pneumothorax condition.

Figure 3B:
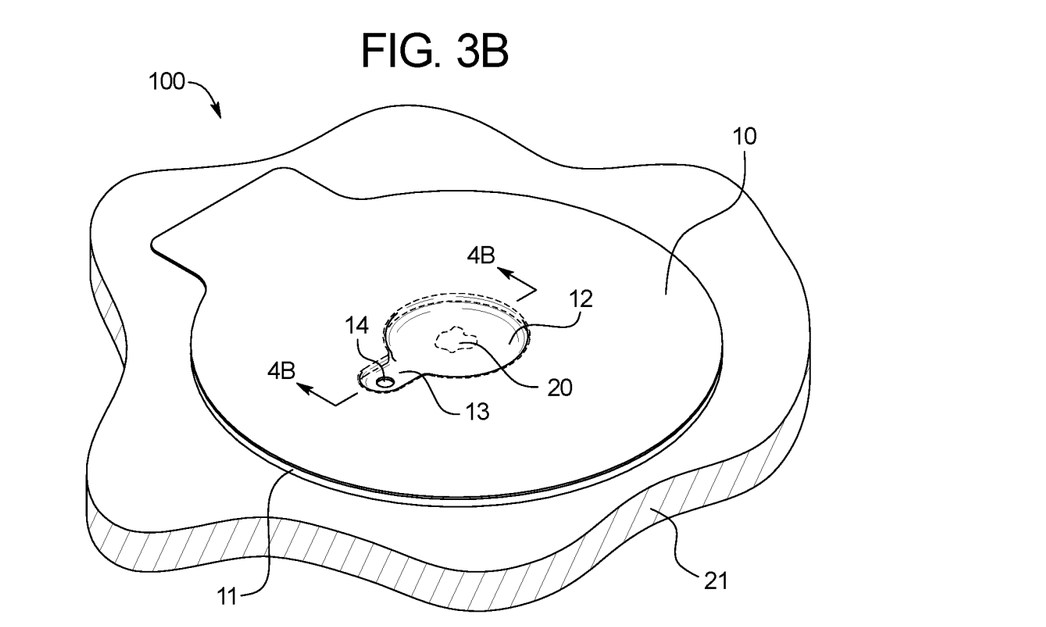
FIG. 3B illustrates an isometric view of the chest wound seal applied to a penetrating chest wound and preventing air from entering the wound through the closed one-way valve during inhalation.
Figure 4B:
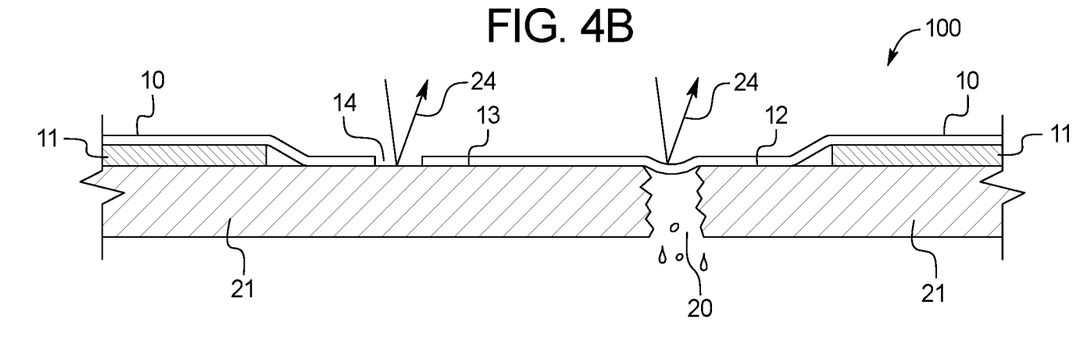
FIG. 4B illustrates a sectional view at an enlarged scale taken along Line 4B-4B of FIG. 3B.

With reference to FIG. 3B and FIG. 4B, the one-way valve of the chest wound seal 100 is shown in its closed state. FIG. 3B illustrates an isometric view of the chest wound seal 100 applied to a penetrating chest wound 20 and preventing air from entering the wound 20 through the closed one-way valve during inhalation. FIG. 4B illustrates a sectional view at an enlarged scale taken along Line 4B-4B of FIG. 3B. Chamber 12 and vent channel 13 are in a closed position, with the thin, flexible backing sheet 10 shown as pushed against the surface of the patient's chest 21 by outside air pressure 24 in response to the negative pressure produced by the patient's lungs during inhalation. The negative pressure is applied to the chamber 12 and vent channel 13 via the penetrating chest wound 20. When the patient changes from exhalation to inhalation the air flow through the one-way valve changes direction and the negative pressure forces the thin, flexible backing sheet 10 to collapse against the surface of the patient's chest 21, thereby sealing the penetrating chest wound 20 in an air tight formation and thereby preventing outside air from entering the patient's pleural space via the penetrating chest wound 20. In an embodiment, the thin, flexible backing sheet 10 is sufficiently compliant that it may also create a functional seal in the presence of small airborne debris on the surface of the patient's chest 21. This tolerance for debris enhances the value of the chest wound seal 100 under conditions where airborne debris is common. The blocking by the one-way valve of outside air from entering the pleural space via the penetrating chest wound 20 results in the prevention of or reduction in severity of the tension pneumothorax condition.

In some embodiments, the chest wound seal 100 may be square instead of round or may be of any appropriate shape necessary for implementing the aforementioned objectives of the chest wound seal 100. In some embodiments, the chest wound seal 100 may be of any appropriate size that provides sufficient adhesive area for securely attaching the chest wound seal 100 to the patient. In some embodiments, the chest wound seal 100 may have one or more vent channels 13. In some embodiments, the chest wound seal 100 may have vent channels 13 at any appropriate orientation angle between the vent channel 13 and the lifting tab 19.

In some embodiments, the vent hole 14 may be of an appropriate size to accommodate the air/fluids necessary. A larger vent hole 14 affords better venting efficiency. However, a vent hole 14 that is too large may affect the strength of the thin, flexible backing sheet due to the amount of material removal. Additionally, a large vent hole 14 could get caught on external items due to its large open area. In an embodiment, the vent hold 14 is approximately one fourth of an inch in width or diameter.

In some embodiments, the vent hole cover 17 may be of any appropriate shape necessary to block the vent hole. In some embodiments, the vent hole cover 17 may be of any appropriate configuration that is easily removed when necessary. In some embodiments, the chest wound seal 12 may include two lifting tabs 19. And, in some embodiments, the hydrogel adhesive sheet 11 may be any other suitable adhesive.

Figure 7:
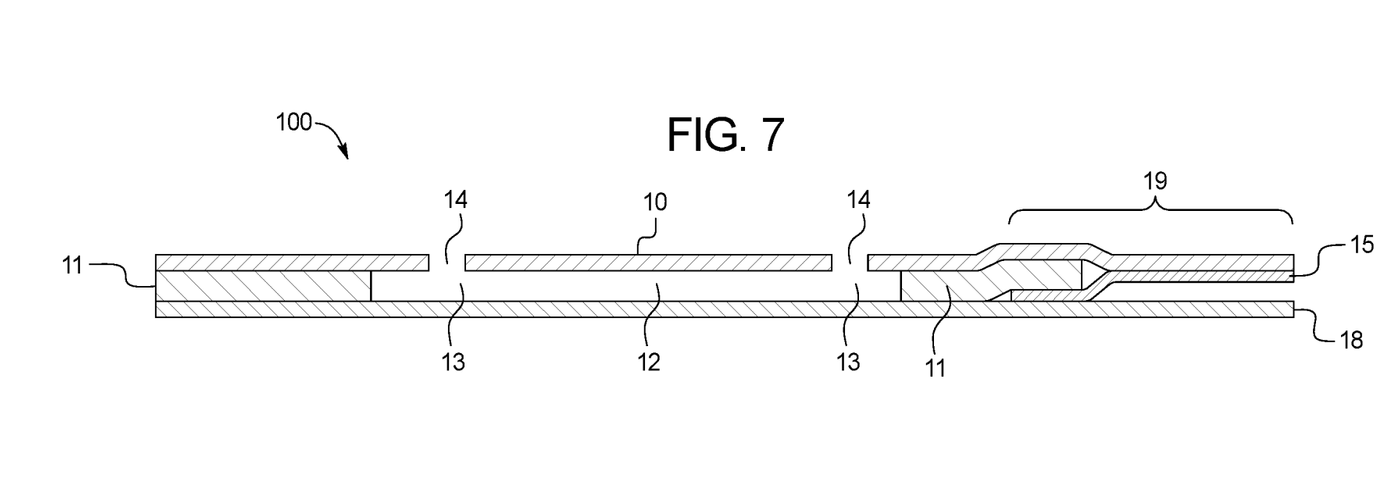
FIG. 7 illustrates a sectional view, not to scale, with some details enlarged to show their details, taken along Line 7-7 of FIG. 6.

With reference to FIG. 6 and FIG. 7, another embodiment of chest wound seal 100 for use as an occlusive dressing for a penetrating chest wound 20 is shown. The chest wound seal 100 may include four vent holes 14 to permit sufficient venting. In the embodiment shown, the vent holes 14 may be arranged in a cross pattern with one of the vent holes 14 oriented toward the lifting tab 19.

In the embodiment shown in FIGS. 6 and 7, the release strip 16 has been eliminated. The adhesive-backed plastic support sheet 15 has applied, adhesive side up, to the bottom surface of the adhesive sheet 11 and to the bottom surface of the lifting tab 19. The adhesive sheet 11 overlaps the plastic support sheet 15 an appropriate distance. In one embodiment, the overlap is one-quarter inch. In the absence of the plastic support sheet 15, when force is applied to the lifting tab 19, the adhesive sheet's adherence to the patient's chest 21 may be stronger than it's adherence to the backing sheet 10 causing the backing sheet 10 and the adhesive sheet to separate. Accordingly, by attaching the plastic support sheet 15 to the adhesive sheet 11 and the lifting tab 19, the plastic support sheet 15 assists in the removal of the adhesive sheet 11 during the removal of the chest wound seal 100 from the patient's chest 21 by encouraging the separation of the adhesive sheet 11 from the patient's chest 21.

The chest wound seal 100 may be fabricated using the elements shown in the exploded view of FIG. 1. The following fabrication sequence is one preferred method. Other fabrication sequences may be followed if the assembly equipment is capable of maintaining the proper alignment between each of the elements of the chest wound seal 100.

First, as shown in the embodiments shown in FIGS. 1 and 6, a thin layer of hydrogel adhesive sheet 11 gets modified to remove hydrogel from the cutout area that will be used as the chamber 12 and the vent channels 13. The hydrogel adhesive sheet 11 may be cut to the generally round chest wound seal 100 shape or that cut may be made later.

Second, as shown in FIG. 6, the hydrogel adhesive sheet 11 gets applied to the bottom surface of the thin, flexible backing sheet 10.

Third, in the embodiment shown in FIG. 6, the adhesive-backed plastic support sheet 15 gets applied, adhesive side up, to the bottom surface of the hydrogel adhesive sheet 11 and to the bottom surface of the lifting tab 19. The hydrogel adhesive sheet 11 will overlap the lifting tab 19 an appropriate distance. In one embodiment, the overlap is one-quarter inch.

To fabricate the embodiment shown in FIG. 1, an alternate fabrication sequence is provided after the hydrogel adhesive sheet is modified to remove hydrogel from the cutout area. The alternate fabrication sequence replaces the second and third steps above. First, the adhesive-backed plastic support sheet 15 gets applied, adhesive side up, to the bottom surface of the lifting tab 19 of the flexible backing sheet 10. Next, the hydrogel adhesive sheet 11 gets applied to the bottom surface of the thin, flexible backing sheet and the bottom surface of the adhesive-backed plastic support sheet 15. The hydrogel will overlap the plastic support sheet 15 an appropriate distance. In one embodiment the overlap is one-quarter inch. Next, the narrow strip of plastic sheet that will be used as a release strip 16 gets applied over the bottom surface of the edge of the hydrogel adhesive of the adhesive sheet 11 where the hydrogel overlaps the lifting tab 19.

Fourth, in the embodiments shown in FIGS. 1 and 6, the vent holes 14 get cut in the thin, flexible plastic sheet 11, with the center of the vent holes 14 nominally coincident with the center of curvature of the half-round hydrogel cutout at the end of the vent channels 13. The vent holes 14 may be cut before the hydrogel adhesive sheet is applied, if the fabrication equipment is capable of maintaining the proper alignment between the hole and the hydrogel adhesive cutout of the vent channel 13.

Fifth, in the embodiments shown in FIGS. 1 and 6, the plastic sheet that will be used as the removable release liner 18 gets applied to the bottom surface of the hydrogel adhesive sheet 11.

If a different fabrication sequence is followed, the vent holes 14 may be cut after the addition of the removable release liner 18. In this case, the cutting of the vent holes 14 may also cut a like hole in the removable release liner 18.

Next, if the vent hole covers 17 are to be included, the vent hole covers 17 get added to the top surface of the thin, flexible backing sheet 10, in a location sufficient to block the vent holes 14.

Finally, the assembled chest wound seal 100 gets cut to the desired exterior dimensions. In some embodiments, each of the various layers and components of the chest wound seal 100 may be cut prior to assembly, if the assembly equipment is capable of maintaining the proper alignment between all of the layers and components.

The chest wound seal 100 is described using technology and materials available at the time of disclosure. This does not preclude future technological advancements from being included as part of the chest wound seal 100. In language used herein, objects described in the singular may be provided in the plural and objects described in the plural may be provided in the singular.

The terms, expressions, descriptions, and embodiments employed here are used for purposes of description and illustration and not of limitation. It is to be understood that changes, variations, and alternative embodiments may be made without departing from the spirit or scope of the claims.

It should be noted that various changes and modifications to the presently preferred embodiments described herein will be apparent to those skilled in the art. Such changes and modifications may be made without departing from the spirit and scope of the present invention and without diminishing its attendant advantages.

We claim:

1. A vented chest wound seal for a penetrating chest wound comprising:
    a flexible sheet including a top surface and a bottom surface;
    an adhesive hydrogel layer covering a portion of the bottom surface of the flexible sheet, the adhesive hydrogel layer including an inner perimeter and an outer perimeter, the outer perimeter forming a continuous perimeter of hydrogel along the bottom surface of the flexible sheet; and
    a plurality of vent channels, each including a first opening to a space inside of the inner perimeter, extending radially outward to an outer terminal end venting to the top surface of the flexible sheet, wherein the outer terminal end is spaced apart from the outer perimeter of the adhesive hydrogel layer towards the space.

2. The chest wound seal of claim 1, further including:
    a lifting tab integrally formed with the flexible sheet;
    a plastic support sheet secured to the lifting tab to provide support; and
    a narrow release strip applied over a bottom surface of an edge of the adhesive layer closest to the lifting tab.

3. The chest wound seal of claim 1, further including:
    a lifting tab integrally formed with the flexible sheet;
    a plastic support sheet secured to the lifting tab to provide support;
    wherein a portion of the plastic support sheet is applied over a bottom surface of an edge of the adhesive hydrogel layer closest to the lifting tab.

4. The chest wound seal of claim 1, further including a vent hole cover, wherein the vent hole cover includes an adhesive surface and a pull tab, wherein the adhesive surface secures the vent hole cover over the terminal ends of the plurality of vent channels.

5. The chest wound seal of claim 1, wherein a width between the outer perimeter and the terminal ends of the plurality of vent channels is one-half inch or greater.

6. The chest wound seal of claim 5, wherein the width between the outer perimeter and the terminal ends of the plurality of vent channels is approximately one-inch.

7. A vented chest wound seal for a penetrating chest wound consisting of:
    a flexible sheet including a top surface and a bottom surface;
    an adhesive hydrogel layer covering a portion of the bottom surface of the flexible sheet, the adhesive hydrogel layer including an inner perimeter and an outer perimeter, the outer perimeter forming a continuous perimeter of hydrogel along a bottom surface of the flexible sheet; and
    and a vent channel extending through the flexible sheet from the bottom surface to the top surface, the vent channel including a first opening to a space inside of the inner perimeter, extending radially outward from a central portion of the space to an outer terminal end venting to the top surface of the flexible sheet, wherein the outer terminal end is spaced apart from the outer perimeter of the adhesive hydrogel layer towards the central portion of the space.

8. The vented chest wound seal of claim 7 wherein there are at least four vent channels extending through the flexible sheet to the top surface, each of the vent channels including a first opening to a space inside of the inner perimeter, extending radially outward from a central portion of the space to an outer terminal end venting to the top surface of the flexible sheet, wherein the outer terminal end is spaced apart from the outer perimeter of the adhesive hydrogel layer towards the central portion of the space.

9. The chest wound seal of claim 8, further including:
    a lifting tab integrally formed with the flexible sheet;
    a plastic support sheet secured to the lifting tab to provide support; and
    a narrow release strip applied over a bottom surface of an edge of the adhesive layer closest to the lifting tab.

10. The chest wound seal of claim 8, further including:
    a lifting tab integrally formed with the flexible sheet;
    a plastic support sheet secured to the lifting tab to provide support;
    wherein a portion of the plastic support sheet is applied over a bottom surface of an edge of the adhesive hydrogel layer closest to the lifting tab.

11. The chest wound seal of claim 7, further including a vent hole cover, wherein the vent hole cover includes an adhesive surface and a pull tab, wherein the adhesive surface secures the vent hole cover over the terminal end of the vent channels.

12. The chest wound seal of claim 7, wherein a width between the outer perimeter and the terminal end is one-half inch or greater.

13. The chest wound seal of claim 12, wherein the width between the outer perimeter and the terminal end is approximately one-inch.

* * * * *